(12) United States Patent
Li et al.

(10) Patent No.: US 7,392,092 B2
(45) Date of Patent: Jun. 24, 2008

(54) METHOD AND APPARATUS FOR OPERATING A DIVERSITY ANTENNA SYSTEM FOR COMMUNICATING WITH IMPLANTABLE MEDICAL DEVICE

(75) Inventors: Hui Li, Maple Grove, MN (US); Joseph E. Bange, Eagan, MN (US); Sylvia Quiles, Edina, MN (US); Prashant Rawat, Blaine, MN (US); Vineel Vallapureddy, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 170 days.

(21) Appl. No.: 11/068,476

(22) Filed: Feb. 28, 2005

(65) Prior Publication Data

US 2006/0195161 A1 Aug. 31, 2006

(51) Int. Cl.
H04B 7/04 (2006.01)
(52) U.S. Cl. .......................................... 607/60; 607/32
(58) Field of Classification Search ................... 607/60, 607/32; 128/903
See application file for complete search history.

(56) References Cited

U.S. PATENT DOCUMENTS

| | | | |
|---|---|---|---|
| 5,142,534 A | 8/1992 | Simpson et al. | |
| 5,342,408 A | 8/1994 | deCoriolis et al. | |
| 6,167,312 A | 12/2000 | Goedeke | |
| 6,169,925 B1 | 1/2001 | Villaseca et al. | |
| 6,434,429 B1 * | 8/2002 | Kraus et al. ................... | 607/60 |
| 6,574,510 B2 | 6/2003 | Von Arx et al. | |
| 7,069,086 B2 | 6/2006 | Von Arx | |
| 7,072,718 B2 | 7/2006 | Von Arx et al. | |
| 2003/0114897 A1 | 6/2003 | Von Arx et al. | |
| 2004/0106967 A1 | 6/2004 | Von Arx et al. | |
| 2004/0212496 A1 | 10/2004 | Villaseca et al. | |
| 2004/0260363 A1 | 12/2004 | Arx et al. | |
| 2005/0222629 A1 | 10/2005 | Perschbacher et al. | |
| 2005/0283208 A1 | 12/2005 | Von Arx et al. | |
| 2006/0009818 A1 | 1/2006 | Von Arx et al. | |
| 2006/0030903 A1 | 2/2006 | Seeberger et al. | |
| 2006/0111643 A1 | 5/2006 | Cazares et al. | |

(Continued)

FOREIGN PATENT DOCUMENTS

EP    0744841 A2    11/1996

(Continued)

OTHER PUBLICATIONS

"International Search Report and Written Opinion for Application No. PCT/US2006/007092, dated Aug. 17, 2006", 16 Pages.

*Primary Examiner*—Kennedy J. Schaetzle
(74) *Attorney, Agent, or Firm*—Schwegman, Lundberg & Woessner, P.A.

(57) ABSTRACT

A far-field radio frequency (RF) telemetry system for communicating with an implantable medical device includes a diversity antenna system. Multi-frame messages each including multiple outgoing data frames are transmitted to the implantable medical device. In response, the implantable medical device transmits response data frames each following one or more of the outgoing data frames, according to a predetermined communication protocol. An antenna control circuit selects an antenna of the diversity antenna system for transmitting the outgoing data frames and/or receiving the response data frames based the quality of signal reception associated with the response data frames.

36 Claims, 13 Drawing Sheets

U.S. PATENT DOCUMENTS

| | | |
|---|---|---|
| 2006/0161223 A1 | 7/2006 | Vallapureddy et al. |
| 2006/0194615 A1 | 8/2006 | Vallapureddy et al. |
| 2006/0195162 A1 | 8/2006 | Arx et al. |

FOREIGN PATENT DOCUMENTS

| | | |
|---|---|---|
| EP | 0808033 A2 | 11/1997 |
| EP | 0863620 A2 | 8/1998 |
| EP | 0889603 A2 | 1/1999 |
| WO | WO-2005115541 A1 | 12/2005 |
| WO | WO-2006093766 A1 | 9/2006 |
| WO | WO-2006093964 A1 | 9/2006 |

* cited by examiner

METHOD AND APPARATUS FOR OPERATING A DIVERSITY ANTENNA SYSTEM FOR COMMUNICATING WITH IMPLANTABLE MEDICAL DEVICE

CROSS-REFERENCE TO RELATED APPLICATIONS

This application is related to co-pending, commonly assigned, U.S. patent application Ser. No. 11/068,497, entitled "DIVERSITY ANTENNA SYSTEM FOR COMMUNICATION WITH AN IMPLANTABLE MEDICAL DEVICE," filed on Feb. 28, 2005 and U.S. patent application Ser. No. 11/068,478, entitled "METHOD AND APPARATUS FOR ANTENNA SELECTION TN A DIVERSITY ANTENNA SYSTEM FOR COMMUNICATING WITH IMPLANTABLE MEDICAL DEVICE," filed on Feb. 28, 2005, which are hereby incorporated by reference in their entirety.

TECHNICAL FIELD

This document relates generally to telemetry for implantable medical systems and particularly to an external telemetry system having diversity antennas for communicating with an implantable medical device.

BACKGROUND

Medical devices are implanted in human bodies for monitoring physiological conditions, diagnosing diseases, treating diseases, or restoring functions of organs or tissues. Examples of such implantable medical devices include cardiac rhythm management (CRM) devices, neural stimulators, neuromuscular stimulators, drug delivery devices, and biological therapy devices. When an implantable medical device is intended for long-term use in a patient, its size and power consumption are limited by implantability and longevity requirements. Consequently, many implantable medical devices depend on external systems to perform certain functions. Communication between an implantable method device and an external system is performed via telemetry. Examples of specific telemetry functions include programming the implantable medical device to perform certain monitoring or therapeutic tasks, extracting an operational status of the implantable medical device, transmitting realtime physiological data acquired by the implantable medical device, and extracting physiological data acquired by and stored in the implantable medical device.

One type of telemetry between the implantable medical device and the external system is based on inductive coupling between two closely-placed coils using the mutual inductance between these coils. One of the coils is part of the implantable medical device, and the other coil is part of the external system. This type of telemetry is referred to as inductive telemetry or near-field telemetry because the coils must be closely situated for obtaining magnetically coupled communication.

Far-field radio-frequency (RF) telemetry provides another means for communications between the implantable medical device and the external system. The far-field RF telemetry is performed using an RF transceiver in the implantable medical device and an RF transceiver in the external system. The far-field RF telemetry frees the patient from any body surface attachment that limits mobility and is more suitable for use when the patient is at home, without the attendance by the physician or other professional caregiver.

The far-field RF telemetry between the implantable medical device and the external system often operates in an environment where RF electromagnetic waves are reflected from various kinds of surfaces. Destructive interference between the incident and reflective waves results in nulls, where the incident wave and reflected wave cancel out. The far-field RF telemetry link is substantially interrupted when an antenna encounters a null. While such a null is moving and usually transient, the interruption to the telemetry link may last long enough to cause a data transmission error.

Therefore, there is a need for ensuring the quality of far-field RF telemetry between an external system and an implanted device when nulls are present.

SUMMARY

A far-field RF telemetry system for communicating with an implantable medical device includes a diversity antenna system. Multi-frame messages each including multiple outgoing data frames are transmitted to the implantable medical device. In response, the implantable medical device transmits response data frames each following one or more of the outgoing data frames, according to a predetermined communication protocol. An antenna control circuit selects an antenna of the diversity antenna system for transmitting the outgoing data frames and/or receiving the response data frames based the quality of signal reception associated with the response data frames.

In one embodiment, a system for communicating with an implantable medical device includes a diversity antenna system, a transceiver, an antenna interface circuit, and an antenna control circuit. The diversity antenna system includes a plurality of antennas for transmitting an outgoing signal to the implantable medical device and receiving an incoming signal from the implantable medical device. The transceiver transmits outgoing data frames by modulating the outgoing signal and receives incoming data frames by demodulating the incoming signal. The antenna interface circuit includes a switch circuit that connects an antenna of the diversity antenna system to the transceiver according to an antenna selection signal. The antenna control circuit produces the antenna selection signal and includes an incoming signal monitoring timer, an incoming signal monitoring circuit, and an antenna selector. The incoming signal monitoring timer generates incoming signal monitoring signals based on a predetermined communication protocol. The incoming signal monitoring circuit detects at least one measure of quality of the incoming signal in response to each of the incoming signal monitoring signals and produces an indication of quality of the incoming signal. The antenna selector adjusts the antenna selection signal based on the indication of quality of the incoming signal.

In one embodiment, a method for operating a telemetry system communicating with an implantable medical device is provided. A diversity antenna system is used for transmitting an outgoing signal to the implantable medical device and receiving an incoming signal from the implantable medical device. The diversity antenna includes a plurality of antennas. Outgoing data frames are transmitted by modulating the outgoing signal. Incoming data frames are received by demodulating the incoming signal. An antenna of the diversity antenna system is selected to be an active antenna according to an antenna selection signal. Incoming signal monitoring signals are generated based on a predetermined communication protocol. An indication of quality of the incoming signal is produced by detecting at least one measure of quality of the incoming signal in response to each of the incoming signal monitoring signals. The antenna selection signal is adjusted based on the indication of quality of the incoming signal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are not necessarily drawn to scale, like numerals describe similar components throughout the several views. The drawings illustrate generally, by way of example, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses an RF telemetry system for bi-directional communication between an implantable medical device and an external system. The external system includes an external telemetry system that uses a diversity antenna system and an antenna control circuit that selects one or more active antenna of the diversity antenna system to ensure quality of communication. In one embodiment, the antenna control circuit selects one or more active antenna of the diversity antenna system for reducing or minimizing data transmission errors associated with nulls. An active antenna is an antenna that is currently used to transmit and/or receive signals. The antenna control circuit selects the one or more active antenna based on the quality of signal reception of the diversity antenna system. The signals transmitted to the implantable medical device include multi-frame messages each including a plurality of data frames. The implantable medical device transmits response data frames after one or more of these transmitted data frames. The antenna control circuit assesses the quality of signal reception when the response data frames are expected to be received by the external telemetry system according to a communication protocol.

Figure 1:
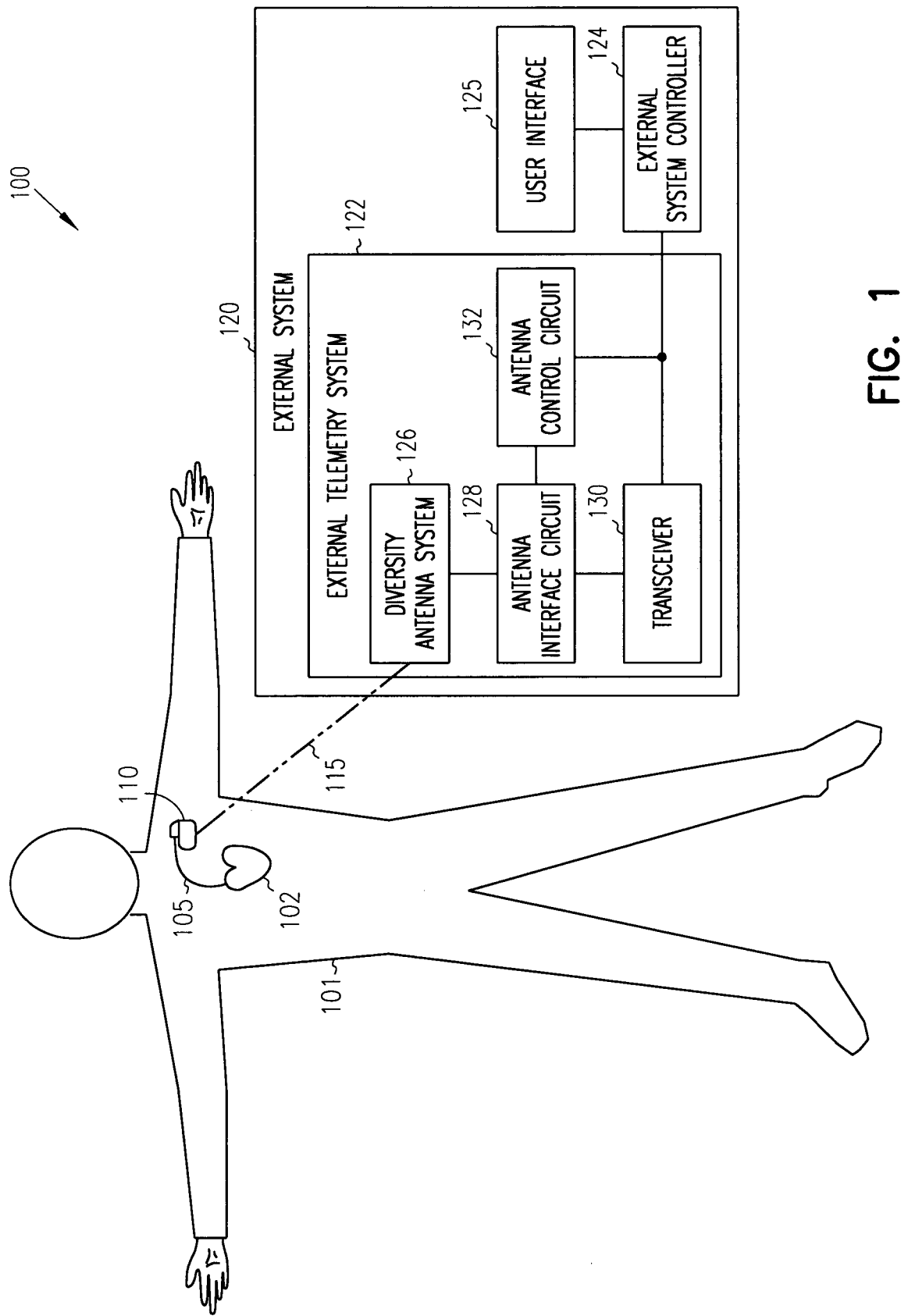
FIG. 1 is an illustration of an embodiment of a CRM system including an implantable medical device and an external system and portions of an environment in which the CRM system is used.

FIG. 1 is an illustration of an embodiment of portions of a CRM system 100 and portions of an environment in which system 100 is used. System 100 includes an implantable medical device 110 and an external system 120. In the illustrated embodiment, after being implanted into a patient's body 101, implantable medical device 110 is coupled to the patient's heart 102 through a lead system 105. Examples of implantable medical device 110 include pacemakers, cardioverter/defibrillators, cardiac resynchronization therapy (CRT) devices, cardiac remodeling control therapy (RCT) devices, neural stimulators, drug delivery systems, biological therapy devices, and patient monitoring devices. External system 120 allows a physician or other caregiver to interact with implantable medical device 110 through an RF telemetry link 115, which provides for bi-directional data communication between implantable medical device 110 and external system 120.

RF telemetry link 115 provides for data transmission from implantable medical device 110 to external system 120. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). RF telemetry link 115 also provides for data transmission from external system 120 to implantable medical device 110. This includes, for example, programming implantable medical device 110 to acquire physiological data, programming implantable medical device 110 to perform at least one self-diagnostic test (such as for a device operational status), and programming implantable medical device 110 to deliver at least one therapy.

RF telemetry link 115 is a far-field telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one embodiment, a communication range of RF telemetry link 115 (a distance over which data is capable of being wirelessly communicated) is at least ten feet but can be as long as allowed by the communication technology utilized. Unlike an inductive telemetry link using a coil placed near implantable medical device 110, attached to the patient, and electrically connected to external system 120 with a cable, using RF telemetry link 115 frees the patient from any physical restraints caused by the coil and the cable and allows external system 120 to be placed entirely away from the sterile filed during an operation such as the implantation of implantable medical device 110.

RF telemetry link 115 is supported by an implant telemetry system of implantable medical device 110 and an external telemetry system 122 of external system 120. External telemetry system 122 includes a diversity antenna system 126, an antenna interface circuit 128, a transceiver 130, and an antenna control circuit 132. Diversity antenna system 126 includes a plurality of antennas to transmit an outgoing signal to implantable medical device 110 and to receive an incoming signal from implantable medical device 110. Antenna interface circuit 128 includes tuning circuitry for diversity antenna system 126 and routes the outgoing and incoming signals between diversity antenna system 126 and transceiver 130. Transceiver 130 transmits outgoing data frames by modulating the outgoing signal and receives incoming data frames by demodulating the incoming signal. The outgoing data frames and the incoming data frames are each a frame being a logic unit of data including a header, a payload, and a trailer. The header includes a "comma," which includes a unique set of bits for signaling a receipt of a frame. A lack of comma, or failure to receive the comma, indicates a failure to receive a frame. The payload includes the data block being transmitted. The trailer includes a cyclic redundancy check (CRC) character having a value generated by a transmitter. A receiver receives that CRC character and also recalculates the CRC character based on the received data block and compares the result to the received CRC character in the trailer. The data is deemed to be correctly transmitted if the recalculated CRC character matches the received CRC character. A CRC error refers to a mismatch between the recalculated CRC character and the received CRC character. Depending on the specific communication formats, the header and the trailer each include additional information for flagging, control of data recovery, and/or synchronization of the receiving device. In various embodiments, the outgoing data frames include multi-frame messages each including a plurality of data frames. The incoming data frames include response frames each being an incoming data frame produced by implantable medical device 110 in response to one or more outgoing data frames. Antenna control circuit 132 controls the operation of antenna interface circuit for an approximately optimal performance, or at least an acceptable performance, of diversity antenna system 126. In various embodiments, antenna control circuit 132 selects an active antenna of diversity antenna system 126 based on the quality of the incoming signal. Such quality is measured by, for example, strength of the incoming signal and/or integrity of the incoming data frames. Antenna control circuit 132 controls the timing for assessing the quality of the incoming signal based on a predetermined communication protocol according to which bi-directional communication is performed via RF telemetry link 115. In one embodiment, antenna control circuit 132 selects a different active antenna of diversity antenna system 126 in response to the detection of a transmission failure in the incoming signal. Such a transmission failure may be associated with a null or an antenna that is damaged or otherwise with a degraded performance. External telemetry system 122 is connected to an external system controller 124, which allows external system 120 to receive information acquired by implantable medical device 110 and to control the operation of implantable medical device 110. External system controller 124 receives the incoming data frames from transceiver 130 and sends the outgoing data frames to transceiver 130. A user interface 125 allows the physician or other caregiver to view the received information and to enter commands and parameters to control the operation of CRM system 100.

In one embodiment, external system 120 includes a programmer. In another embodiment, as illustrated in FIG. 2, external system 120 includes a patient management system.

Figure 2:
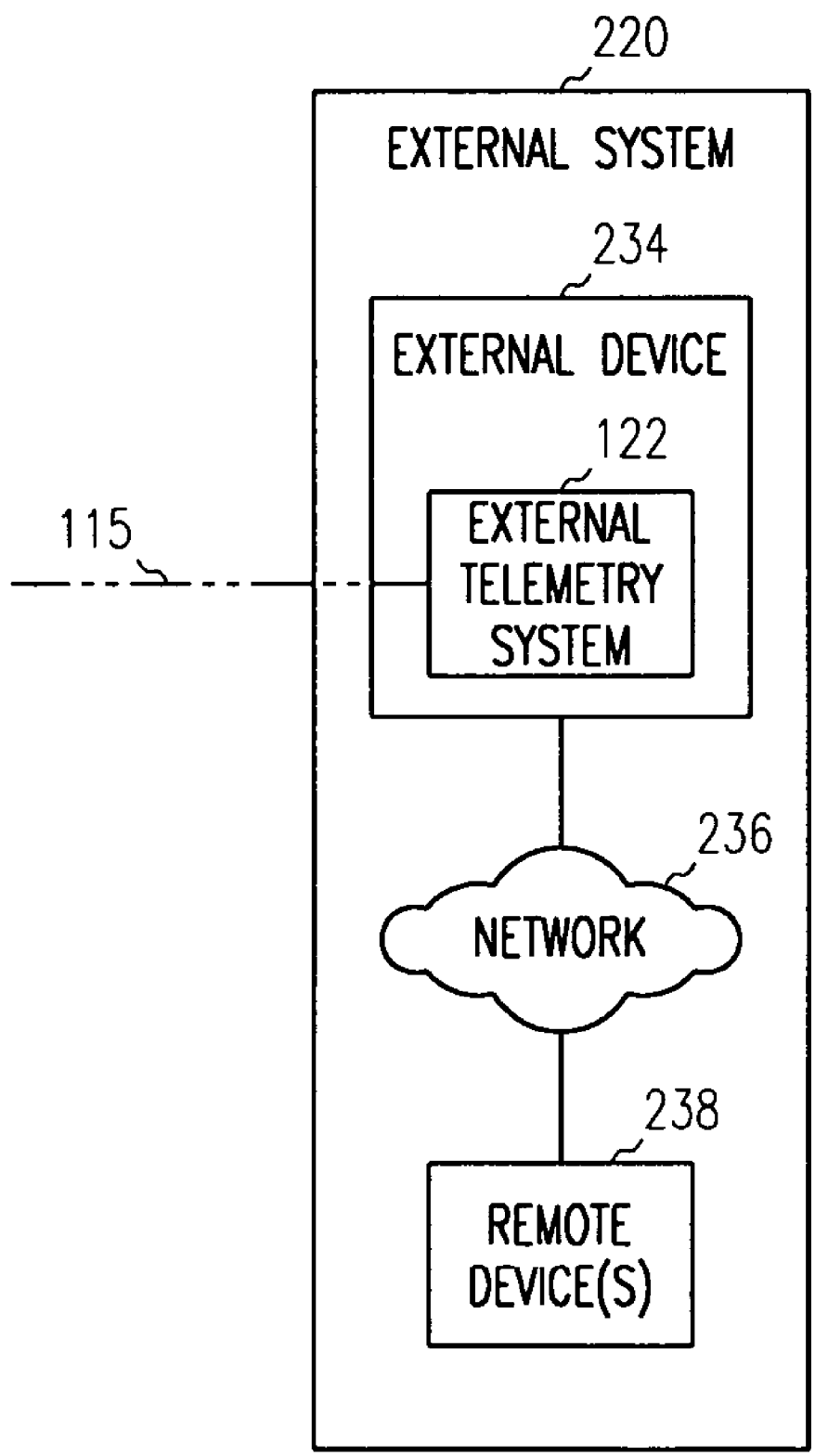
FIG. 2 is a block diagram illustrating a specific embodiment of the external system.

FIG. 2 is a block diagram illustrating an embodiment of external system 220, which is a specific embodiment of external system 120. As illustrated in FIG. 2, external system 220 is a patient management system including an external device 234, a telecommunication network 236, and one or more remote devices 238. External device 234 is placed within the vicinity of implantable medical device 110 and includes external telemetry system 122 to communicate with implantable medical device 110 via RF telemetry link 115. Remote device(s) 238 are in one or more remote locations and communicates with external device 234 through network 236, thus allowing a physician or other caregiver to monitor and treat a patient from a distant location and/or allowing access to various treatment resources from the one or more remote locations.

Figure 3:
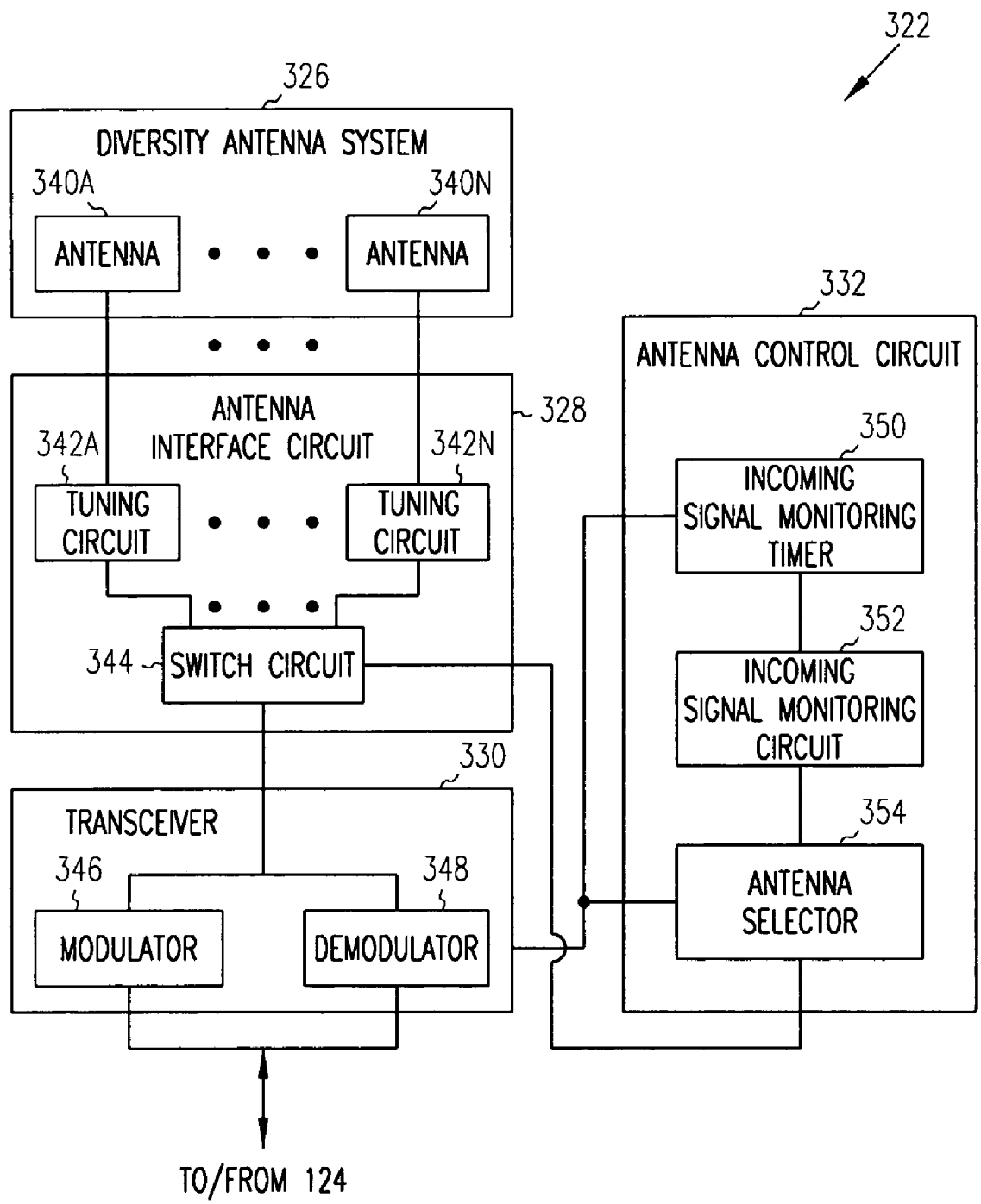
FIG. 3 is a block diagram illustrating an embodiment of a telemetry system of the external system.

FIG. 3 is a block diagram illustrating an embodiment of an external telemetry system 322, which is a specific embodiment of external telemetry system 122. External telemetry system 322 includes a diversity antenna system 326, an antenna interface circuit 328, a transceiver 330, and an antenna control circuit 332.

Diversity antenna system 326 is a specific embodiment of diversity antenna system 126 and includes two or more antennas 340A-N. Each of antennas 340A-N allows for transmitting an outgoing signal to implantable medical device 110 and/or receiving an incoming signal from implantable medical device 110. In one embodiment, diversity antenna system 126 includes two antennas. In a specific embodiment, the two antennas are mounted onto a chassis of an external device such as the programmer or external device 234. In other embodiments, diversity antenna system 126 includes three or more antennas. One example of diversity antenna system 126 is discussed in U.S. patent application Ser. No. 11/068,497, entitled "DIVERSITY ANTENNA SYSTEM FOR COMMUNICATION WITH AN IMPLANTABLE MEDICAL DEVICE," filed on Feb. 28, 2005, which is incorporated by reference herein in its entirety.

Antenna interface circuit 328 is a specific embodiment of antenna interface circuit 128 and includes tuning circuits 342A-N and a switch circuit 344. Tuning circuits 342A-N each provide tuning for a corresponding antenna of antennas 342A-N. Switch circuit 344 provides for a controllable connection between an antenna of diversity antenna system 326 and transceiver 330 according to an antenna selection signal. This antenna is used for transmitting the outgoing signal and receiving the incoming signal. In one embodiment, switch circuit 344 substantially completes the change of the connection from between an antenna of diversity antenna system 326 and transceiver 330 to between another antenna of diversity antenna system 326 and transceiver 330 in about 50 microseconds to 1 millisecond.

Transceiver 330 is a specific embodiment of transceiver 130 and includes a modulator 346 and a demodulator 348. Modulator 346 produces the outgoing signal by modulating an RF carrier with the outgoing data frames, including outgoing data frames that form the multi-frame messages. In one embodiment, the frequency of the RF carrier for the outgoing signal is in a range of approximately 902 MHz to 928 MHz, with approximately 914 MHz being a specific example. The data transmission rate for the outgoing signal is in a range of approximately 60 kilobits per second to 500 kilobits per second, with approximately 204.8 kilobits per second being a specific example. Demodulator 348 recovers the incoming data frames by demodulating the received incoming signal. The implant telemetry circuit of implantable medical device 110 produces the incoming signal by modulating another RF carrier with the incoming data frames. In one embodiment, the frequency of the RF carrier for the incoming signal is in a range of approximately 902 MHz to 928 MHz, with approximately 914 MHz being a specific example. The data transmission rate for the incoming signal is in a range of approximately 60 kilobits per second to 500 kilobits per second, with approximately 102.4 kilobits per second being a specific example. The incoming data frames include the response frames each follow one or more of the outgoing data frames. In one embodiment, amplitude-shift-keying (ASK) is the modulation scheme used for both the outgoing signal and the incoming signal. Modulator 346 is an ASK modulator, and demodulator 348 is an ASK demodulator.

Antenna control circuit 332 is a specific embodiment of antenna control circuit 132 and produces the antenna selection signal. Antenna control circuit 332 includes an incoming signal monitoring timer 350, an incoming signal monitoring circuit 352, and an antenna selector 354. Incoming signal monitoring timer 350 generates incoming signal monitoring signals based on the predetermined communication protocol. The communication protocol specifies the timing for the transmission of the outgoing data frames and timing for the receipt of the incoming data frames. The incoming signal monitoring signals each allow the quality of the incoming signal to be assessed when an incoming data frame is scheduled to be received. Incoming signal monitoring circuit 352 produces an indication of the quality of the incoming signal by detecting at least one measure of quality of the incoming signal in response to each of the incoming signal monitoring signals. Examples of the measure of quality include existence of data transmission error in the incoming signal and strength of the incoming signal. Antenna selector 354 adjusts the antenna selection signal based on the indication of quality of the incoming signal. In one embodiment, antenna selector 354 adjusts the antenna selection signal for connecting a different antenna of diversity antenna system 326 to transceiver 330 when an expected incoming data frame is not detected within a scheduled reception time window. In another embodiment, antenna selector 354 adjusts the antenna selection signal for connecting a different antenna of diversity antenna system 326 to transceiver 330 when a transmission error is detected from the incoming signal. In another embodiment, antenna selector 354 adjusts the antenna selection signal for connecting an antenna of diversity antenna system 326 to transceiver 330 based the strength of the incoming signal associated with each antenna of diversity antenna system 326.

Figure 4:
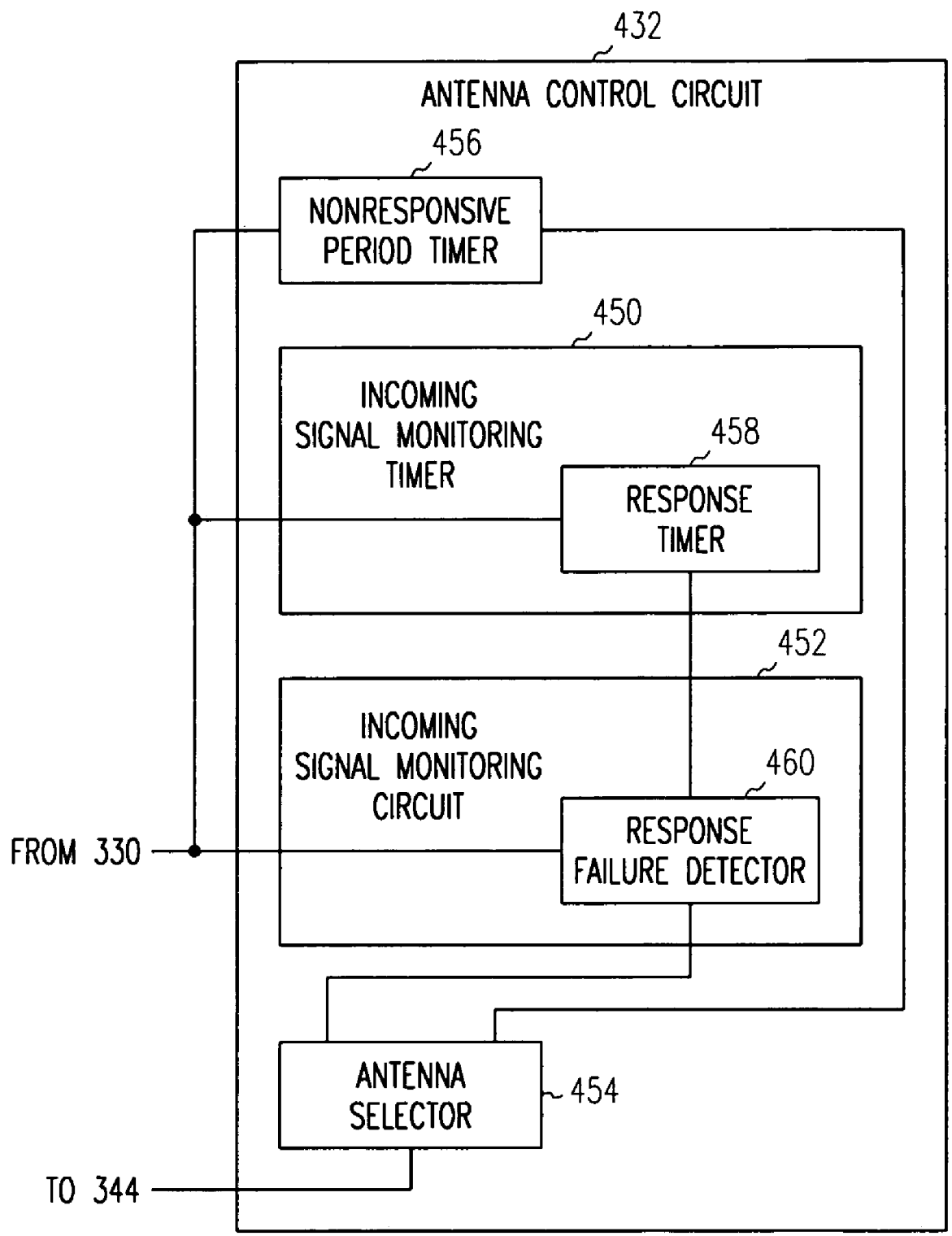
FIG. 4 is a block diagram illustrating an embodiment of an antenna control circuit of the telemetry system.

FIG. 4 is a block diagram illustrating an embodiment of an antenna control circuit 432, which is a specific embodiment of antenna control circuit 332. Antenna control circuit 432 includes a nonresponsive period timer 456, an incoming signal monitoring timer 450, an incoming signal monitoring circuit 452, and an antenna selector 454.

Nonresponsive period timer 456 starts a nonresponsive period during the transmission of a multi-frame message when a response frame is expected to be received according to the predetermined communication protocol. The multi-frame message is transmitted with an active antenna of diversity antenna system 326 connected to transceiver 330. The response frame is expected to be received after several outgoing data frames of the multi-frame message are transmitted, according to the predetermined communication protocol. The nonresponsive period is the maximum time interval allowed for adjusting the antenna selection signal without resulting in a receipt of any response frame without data transmission error. If the nonresponsive period expires without finding another active antenna that provides for acceptable signal quality of the incoming signal, the transmission of the multi-frame message is repeated using a different active antenna, i.e., an antenna that is different from the one with which the transmission of the multi-frame message first started. In one embodiment, the nonresponsive period is a predetermined time interval in a range of approximately 50 milliseconds to one second, with approximately 100 milliseconds being a specific example.

Incoming signal monitoring timer 450 is a specific embodiment of incoming signal monitoring timer 350 and includes a response timer 458. Response timer 458 starts a response time interval during the transmission of the multi-frame message when the response frame is expected to be received and when one or more subsequent response frames, if any, are expected to be received, according to the predetermined communication protocol. In other words, response timer 458 times response time intervals each representing a time window during which a response frame is expected to be received. In one embodiment, the response time interval is a predetermined time interval in a range of approximately 4 milliseconds to 1 second, with approximately 100 milliseconds being a specific example. In one embodiment, the response time interval is set to be equal to the interval between the end of the transmission of an outgoing data frame and the beginning of the transmission of the next outgoing data frame.

Incoming signal monitoring circuit 452 is a specific embodiment of incoming signal monitoring circuit 352 and includes a response failure detector 460. After response timer 458 starts a response time interval, response failure detector 460 detects a response failure during the response time interval. The response failure is a data transmission error associated with a response frame. Examples of such a data transmission error include a failure to receive the response frame, a failure to receive the comma of the response frame, and a CRC error in the response frame. Specific examples of response failure detector 460 are discussed below with reference to FIG. 5.

Antenna selector 454 is a specific embodiment of antenna selector 354. During the nonresponsive period, antenna selector 454 adjusts the antenna selection signal for connecting a different antenna of diversity antenna system 326 to transceiver 330 if the response failure is detected during the predetermined response time interval. If the nonresponsive period expires without any successful receipt of an incoming data frame during the nonresponsive period, antenna selector 454 adjusts the antenna selection signal for connecting a different antenna of diversity antenna system 326 to transceiver 330. Here the different antenna refers to an antenna that is different from the one with which the transmission of the multi-frame message started.

Figure 5:
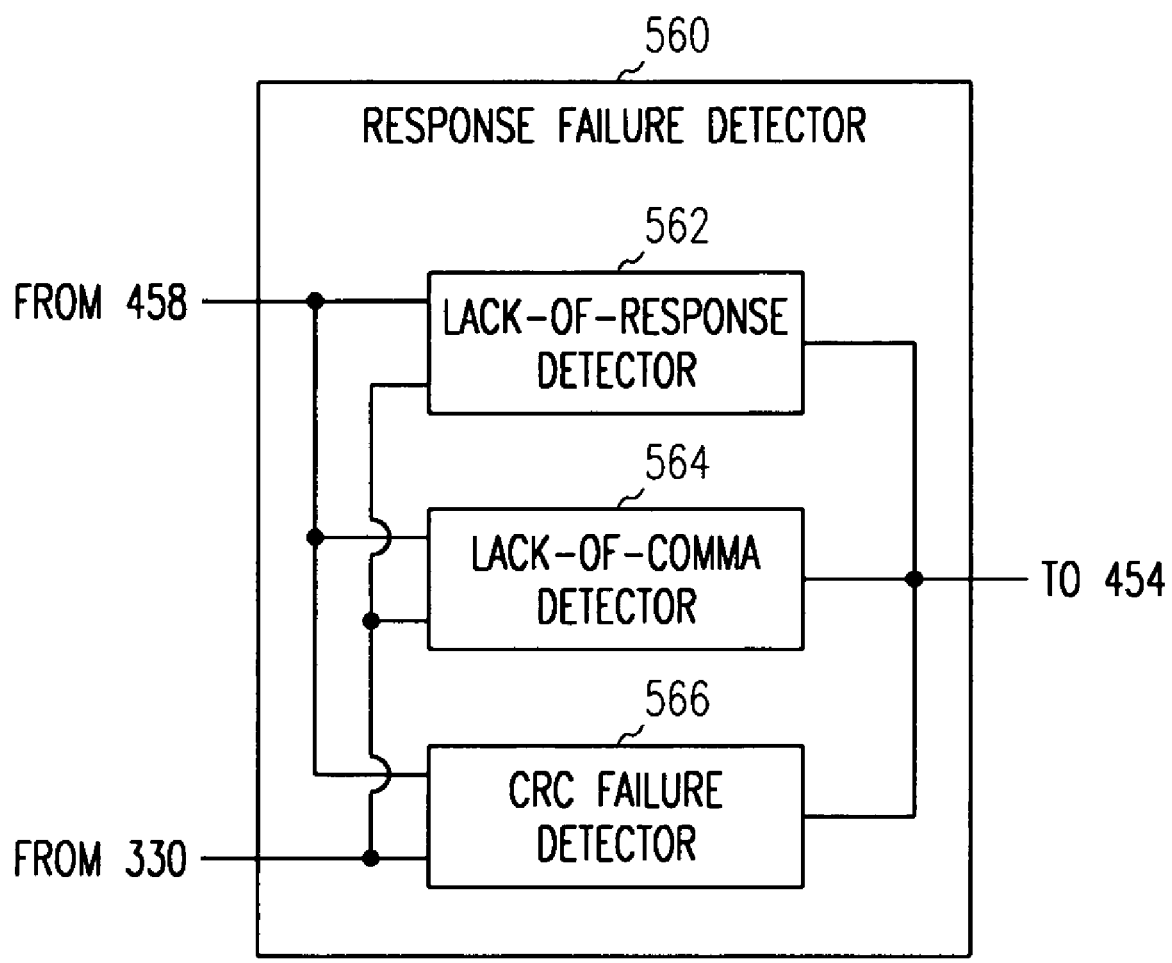
FIG. 5 is a block diagram illustrating an embodiment of a response failure detector of the antenna control circuit of FIG. 4.

FIG. 5 is a block diagram illustrating an embodiment of a response failure detector 560, which is a specific embodiment of response failure detector 460. In one embodiment, as illustrated in FIG. 5, response failure detector 560 includes a lack-of-response detector 562, a lack-of-comma detector 564, and a CRC failure detector 566. In various other embodiments, response failure detector 560 includes any one or more of lack-of-response detector 562, lack-of-comma detector 564, and CRC failure detector 566. The response failure is detected when any one or more of lack-of-response detector 562, lack-of-comma detector 564, and CRC failure detector 566 detect a data transmission error associated with the response frame. Lack-of-response detector 562 detects the response frame during the response time interval. The response failure is detected if no response frame is detected during the response time interval. Lack-of-comma detector 564 detects a comma indicative of a receipt of the response frame during the response time interval. The response failure is detected if the comma is not detected during the response time interval. CRC failure detector 556 detects a CRC failure from the incoming signal during the response time interval. The response failure is detected if the CRC failure is detected during the response time interval.

In other embodiments, response failure detector 560 includes one or more error detectors detecting data transmission errors of types other than the lack of response, the lack of comma, and the CRC failure. Generally, response failure detector 560 detects any predetermined type data transmission error in response frames, with the predetermined type data transmission error representing the response failure.

Figure 6:
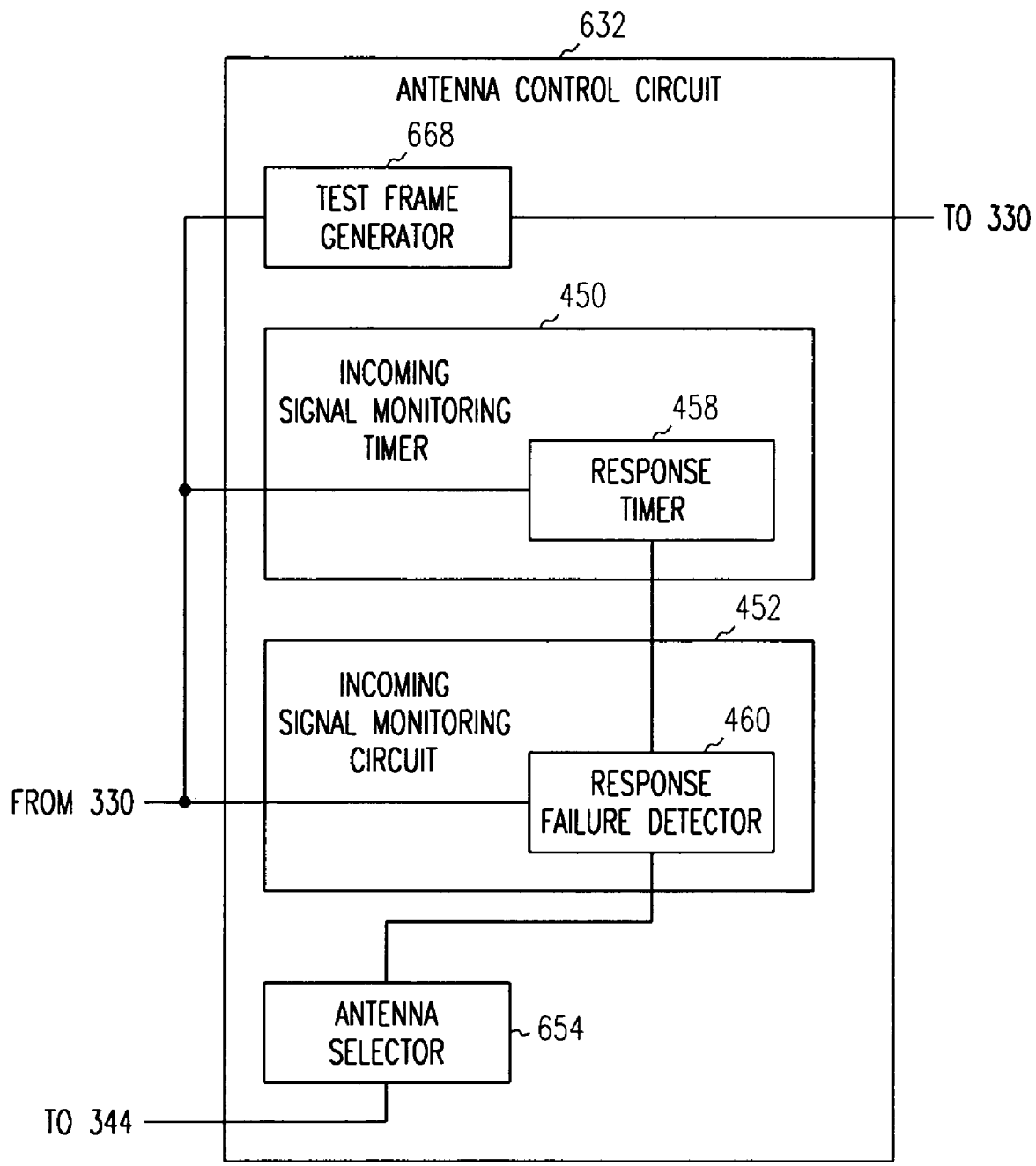
FIG. 6 is a block diagram illustrating another embodiment of the antenna control circuit.

FIG. 6 is a block diagram illustrating an embodiment of an antenna control circuit 632, which is another specific embodiment of antenna control circuit 332. Antenna control circuit 632 includes a test frame generator 668, incoming signal monitoring timer 450, incoming signal monitoring circuit 452, and an antenna selector 654.

Test frame generator 668 produces an antenna test signal prior to the transmission of a multi-frame message. The antenna test signal causes transceiver 330 to transmit a test frame that is an outgoing data frame. Response timer 458 starts the response time interval following the transmission of the test frame. Response failure detector 460 detects the response failure during the response time interval.

Antenna selector 654 is another specific embodiment of antenna selector 354. Antenna selector 654 adjusts the antenna selection signal for connecting a different antenna of diversity antenna system 326 to transceiver 330 when the response failure is detected during the response time interval. In one embodiment, test frame generator 668 produces the antenna test signal for transmitting the test frame using different antennas of diversity antenna system until an antenna associated with an acceptable quality of the incoming signal is found. In another embodiment, if a response failure is detected from an incoming signal received using an antenna, that antenna is deselected as the only antenna associated with an unacceptable quality of the incoming signal. If the response failure is caused by a null encountered by the antenna, the probability that a different antenna also encounters a null is minimal. In one embodiment, test frame generator 668 produces the antenna test signal for transmitting the test frame using different antennas of diversity antenna system until the quality of the incoming signal is assessed for all the antennas of diversity antenna system 326.

Figure 7:
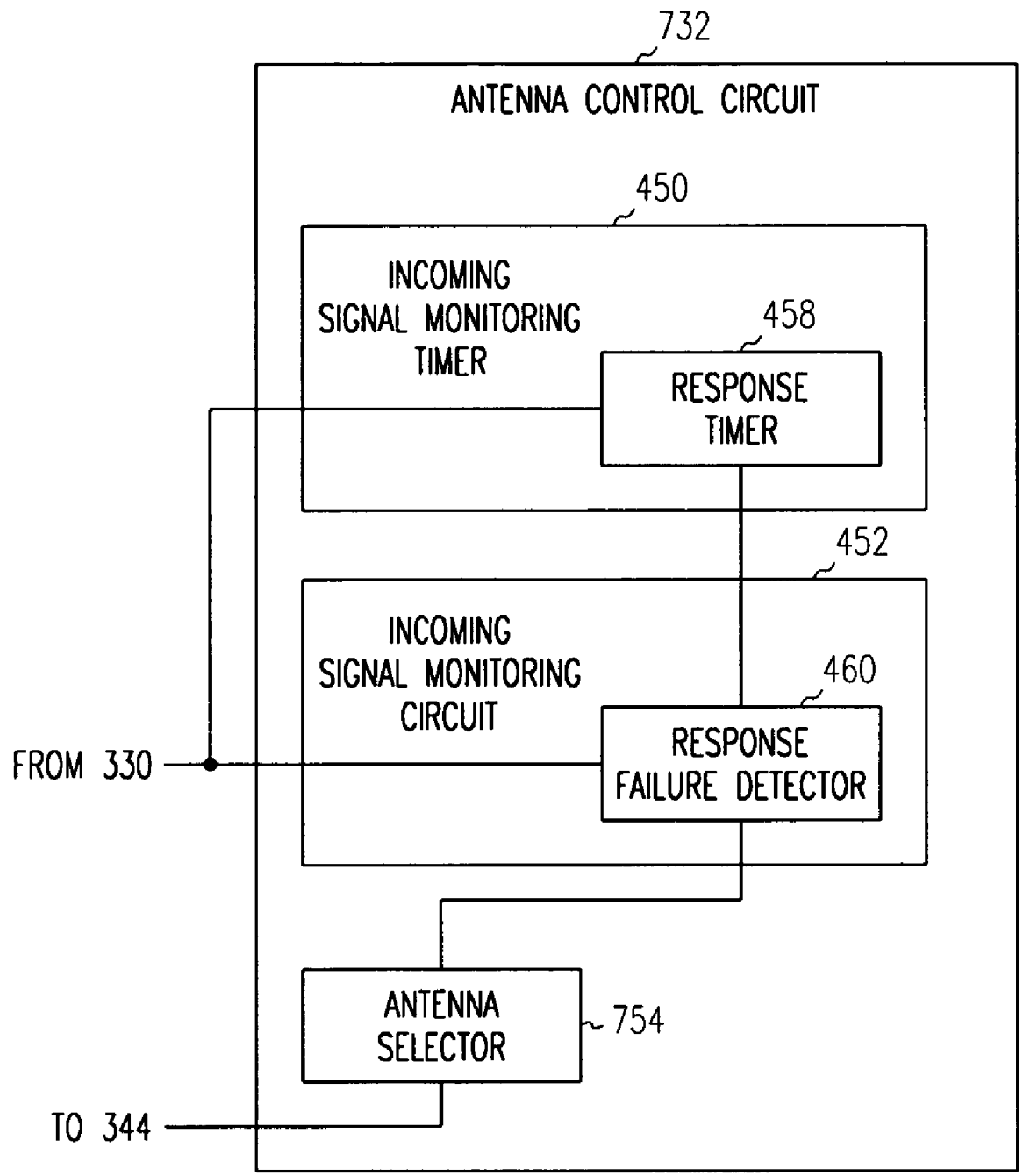
FIG. 7 is a block diagram illustrating another embodiment of the antenna control circuit.

FIG. 7 is a block diagram illustrating an embodiment of an antenna control circuit 732, which is another specific embodiment of antenna control circuit 332. Antenna control circuit 732 includes incoming signal monitoring timer 450, incoming signal monitoring circuit 452, and an antenna selector 754. Response timer 458 times the response time interval when a response frame is expected to be received according to the predetermined communication protocol. Response failure detector 460 detects the response failure during the response time interval.

Antenna selector 754 is another specific embodiment of antenna selector 354. Antenna selector 754 adjusts the antenna selection signal for connecting a different antenna of diversity antenna system 326 to transceiver 330 after the transmission of a multi-frame message if the response failure is detected during the transmission of that multi-frame message. Response failure detector 460 detects the response failure during the transmission of the multi-frame message. When multiple response frames are expected to be received during the transmission of the multi-frame message, a single response failure associated with any of the response frames causes antenna selector 754 to adjust the antenna selection signal for connecting the different antenna of diversity antenna system 326 to transceiver 330. The adjustment of the antenna selection signal occurs following the end of the transmission of the multi-frame message.

Figure 8:
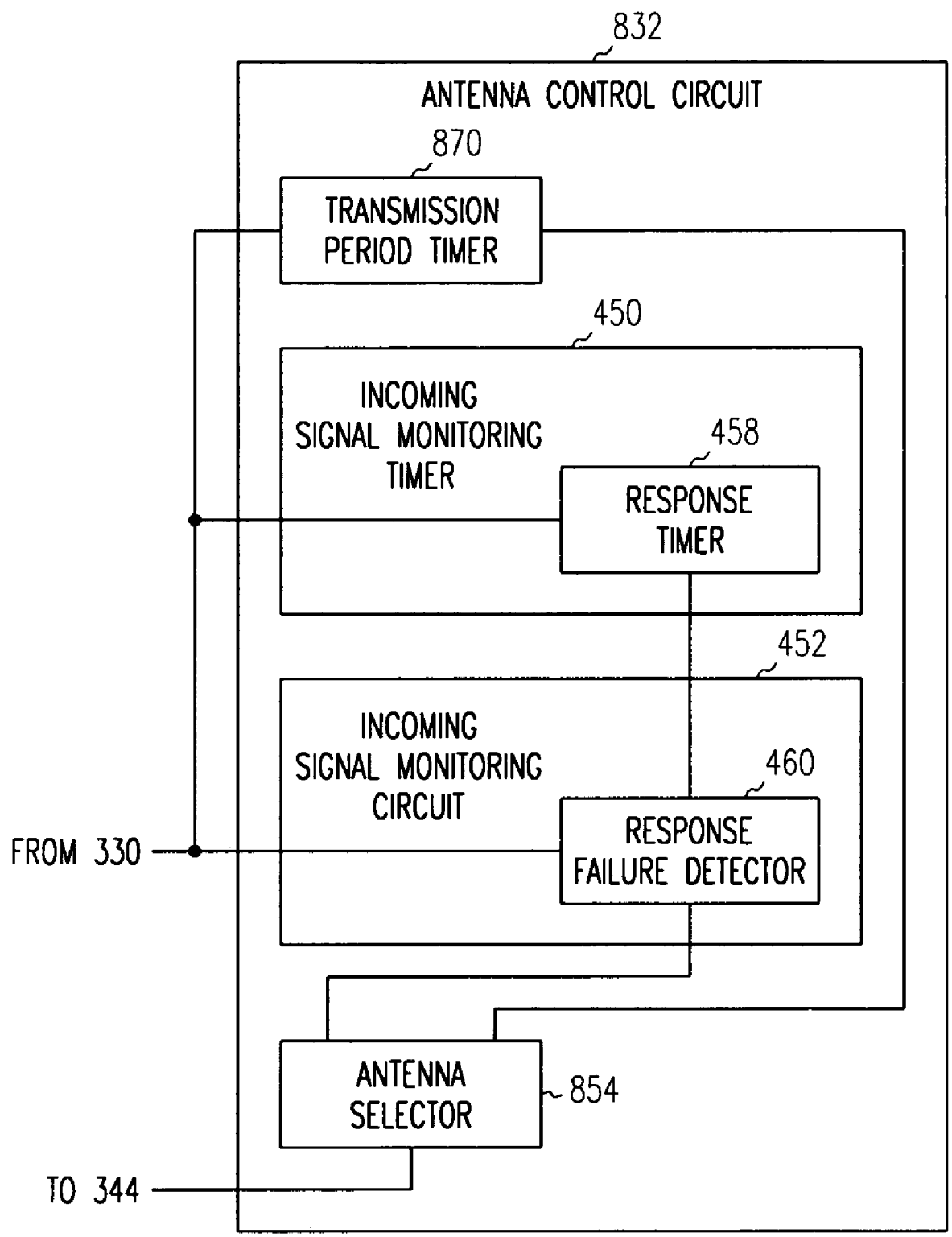
FIG. 8 is a block diagram illustrating another embodiment of the antenna control circuit.

FIG. 8 is a block diagram illustrating an embodiment of an antenna control circuit 832, which is another specific embodiment of antenna control circuit 332. Antenna control circuit 832 includes a transmission period timer 870, incoming signal monitoring timer 450, incoming signal monitoring circuit 452, and an antenna selector 854.

Transmission period timer 870 times transmission periods each including a predetermined number of the outgoing data frames. The transmission period is determined based on the predetermined communication protocol and is specified by the number of the outgoing data frames. The transmission period is long enough such that at least one response frame is expected to be received during each transmission period. For example, if up to five consecutive outgoing data frames may be transmitted without expecting a response frame, the transmission period is determined to include at least six outgoing data frames. Response timer 458 times the response time interval when a response frame is expected to be received according to the predetermined communication protocol. Response failure detector 460 detects the response failure during the response time interval.

Antenna selector 854 is another specific embodiment of antenna selector 354. Antenna selector 854 adjusts the antenna selection signal for connecting a different antenna of diversity antenna system 326 to transceiver 330 at the end of each transmission period if the response failure is detected during that transmission period.

Figure 9:
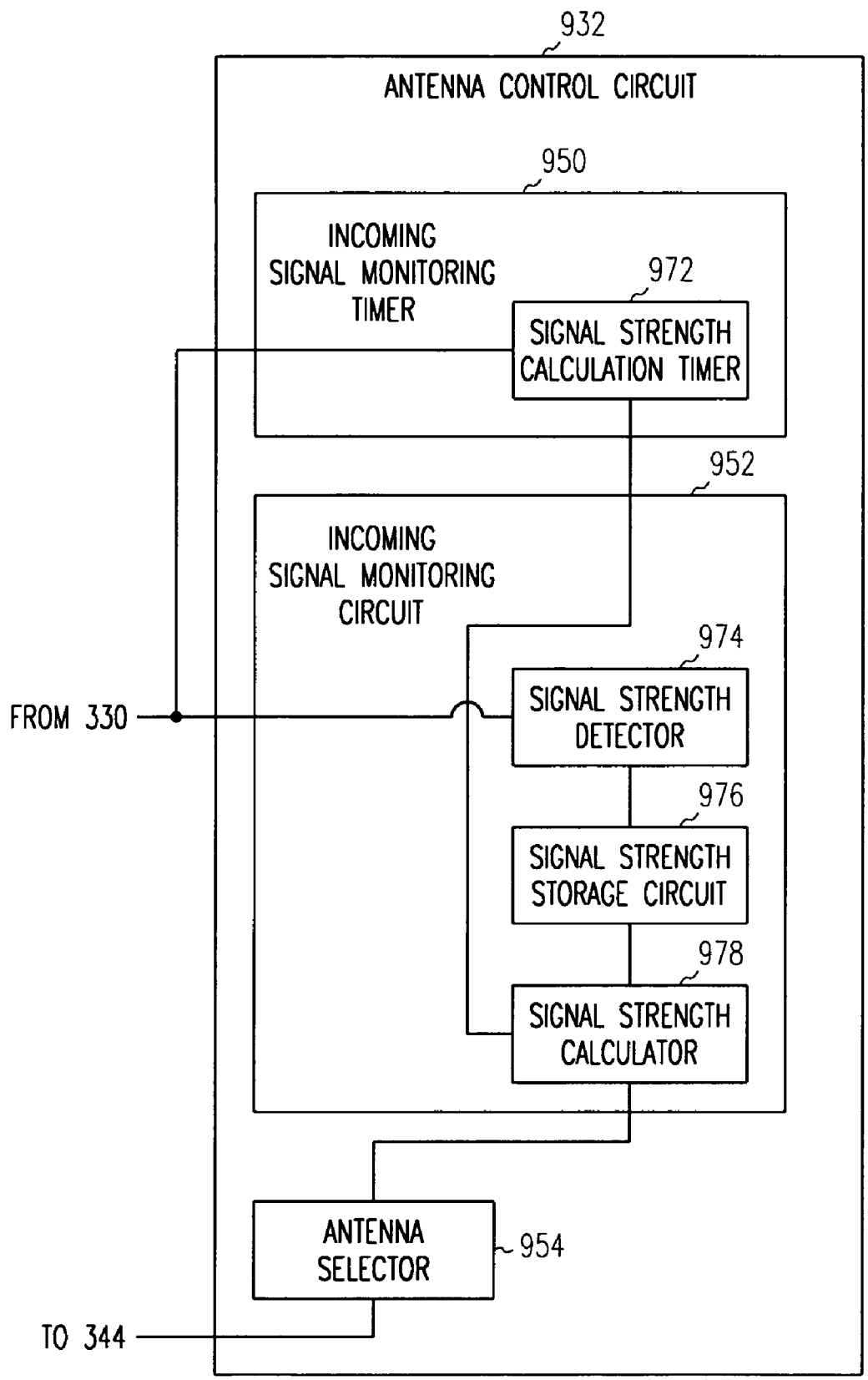
FIG. 9 is a block diagram illustrating another embodiment of the antenna control circuit.

FIG. 9 is a block diagram illustrating an embodiment of an antenna control circuit 932, which is another specific embodiment of antenna control circuit 332. Antenna control circuit 932 includes an incoming signal monitoring timer 950, an incoming signal monitoring circuit 952, and an antenna selector 954.

Incoming signal monitoring timer 950 is another specific embodiment of incoming signal monitoring timer 350 and includes a signal strength calculation timer 972. Signal strength calculation timer 972 generates a signal strength calculation signal prior to the transmission of a multi-frame message.

Incoming signal monitoring circuit 952 is another specific embodiment of incoming signal monitoring circuit 352 and includes a signal strength detector 974, a signal strength storage circuit 976, and a signal strength calculator 978. Signal strength detector 974 measures strength parameters each representing the strength of the incoming signal associated with one antenna of diversity antenna system 326. In one embodiment, signal strength detector 974 measures the strength parameter associated with an antenna each time when that antenna is selected to be the active antenna. Signal strength storage circuit 976 stores the measured strength parameters. Each stored strength parameter is time stamped to indicate when the last measurement of that strength parameter is performed. Signal strength calculator 978 calculates a signal strength index for each antenna of diversity antenna system 326 in response to the signal strength calculation signal. The signal strength index is a function of a stored strength parameter and a weighting factor. The weighting factor is a function of the time elapsed since the last measurement of the strength parameter. A more recently detected strength parameter is given more weight in the calculation of the signal strength index.

Antenna selector 954 is another specific embodiment of antenna selector 354. Antenna selector 954 adjusts the antenna selection signal for connecting an antenna of diversity antenna system 326 to transceiver 330 based on the strength indices calculated for all the antennas of diversity antenna system 326 in response to the signal strength calculation signal. In one embodiment, Antenna selector 954 adjusts the antenna selection signal to select the antenna associated with the highest strength index.

In various embodiments, antenna control circuit 332 may combine one or more of antenna control circuits 432, 632, 732, 832, and 932, as determined by one skilled in the art upon reading and understanding this document. In general, an antenna control circuit assesses the quality of the incoming signal using any viable method and selects an antenna of the diversity antenna system for being the active antenna based on the quality of the incoming signal assessed for this antenna or for a different antenna. In various embodiments, because the probability that two or more antennas of the diversity antenna system simultaneously encounter a null is negligible, when one antenna is indicated to be associated with unacceptable quality of the incoming signal, one or more different antennas are deemed to be associated with acceptable quality of the incoming signal.

In various embodiments, the circuits described in this document are implemented by hardware, software, firmware, or any combination thereof. In various embodiments, the circuits or portions thereof described in this document are each an application-specific circuit constructed to perform one or more particular functions, a general-purpose circuit programmed to perform such function(s), or a combination thereof.

Figure 10:
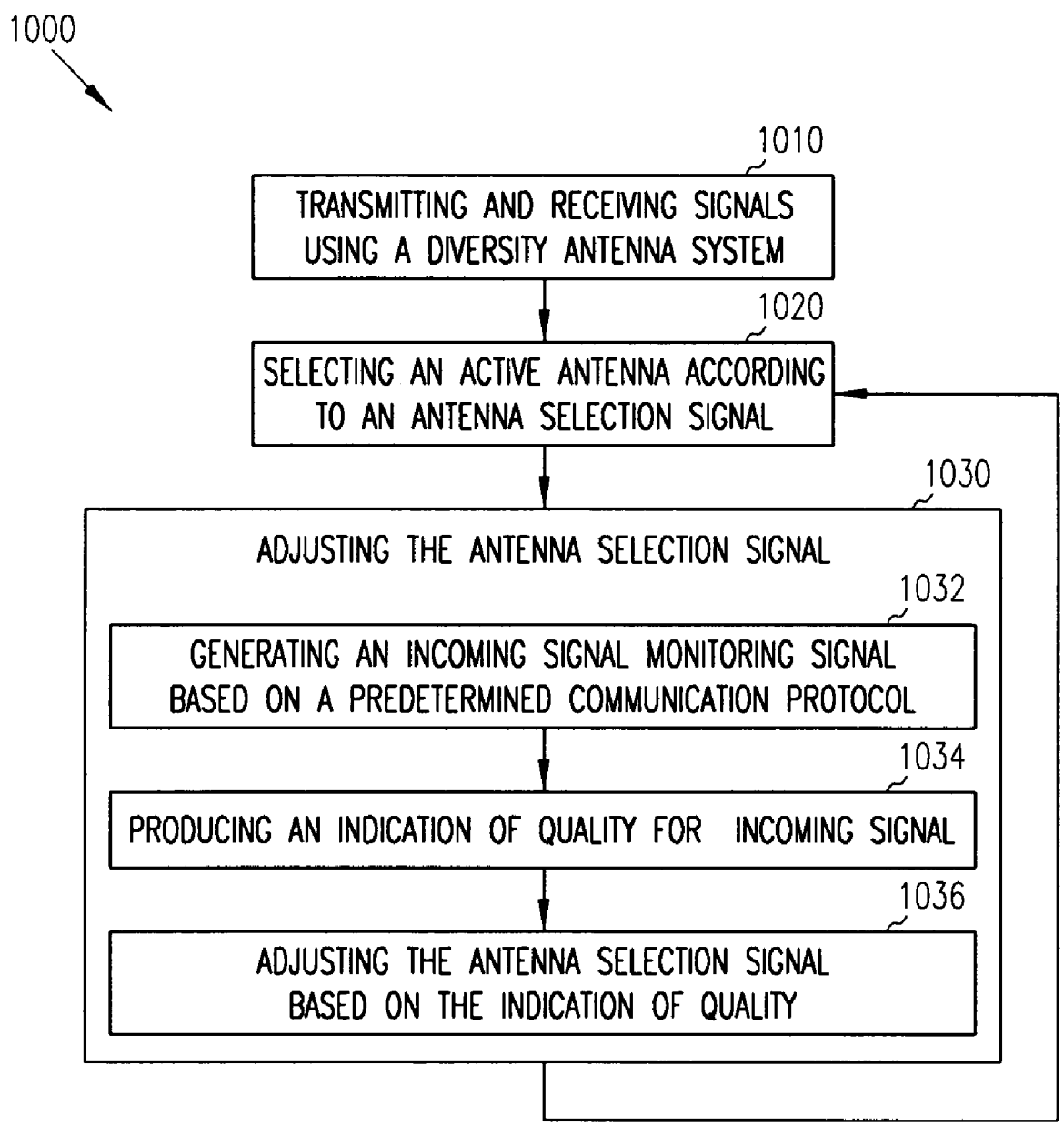
FIG. 10 is a flow chart illustrating an embodiment of a method for operating a telemetry system communicating with an implantable medical device.

FIG. 10 is a flow chart illustrating an embodiment of a method 1000 for operating a telemetry system communicating with an implantable medical device. In one embodiment, the telemetry system includes telemetry system 322.

An outgoing signal is transmitted, and an incoming signal is received, using a diversity antenna system including two or more antennas at 1010. This includes transmitting outgoing data frames to the implantable medical device by modulating the outgoing signal and receiving incoming data frames from the implantable medical device by demodulating the incoming signal. In various embodiments, the transmitted outgoing signal is modulated by multi-frame messages each including a plurality of outgoing data frames. In various embodiments, the multi-frame messages each include two or more outgoing data frames transmitted consecutively without intervening response frames.

An active antenna is selected according to an antenna selection signal at 1020. The active antenna is the antenna that is currently used to transmit the outgoing signal and/or receive the incoming signal. The antenna selection signal specifies which antenna is active.

The antenna selection signal is adjusted based on a measure of quality of the incoming signal at 1030. An incoming signal monitoring signal is generated based on a predetermined communication protocol at 1032. This predetermined communication protocol specifies timing of the transmission of the outgoing data frames and timing of the receipt of the incoming data frames. The incoming signal monitoring signal indicates a time window within which the quality of the incoming signal is to be assessed. An indication of quality is produced for the incoming signal associated with an antenna of the diversity antenna system at 1034, in response to the incoming signal monitoring signal. This indication of quality is produced by detecting at least one measure of quality of the incoming signal, such as presence of a transmission error in the incoming signal and strength of the incoming signal. The antenna selection signal is adjusted based on the indication of quality of the incoming signal at 1036. If the quality of the incoming signal is indicated to be unacceptable, the antenna selection signal is adjusted to select a different antenna of the diversity antenna system to be the active antenna. Exemplary specific embodiments of step 1030 are discussed below with reference to FIGS. 11-15.

Figure 11:
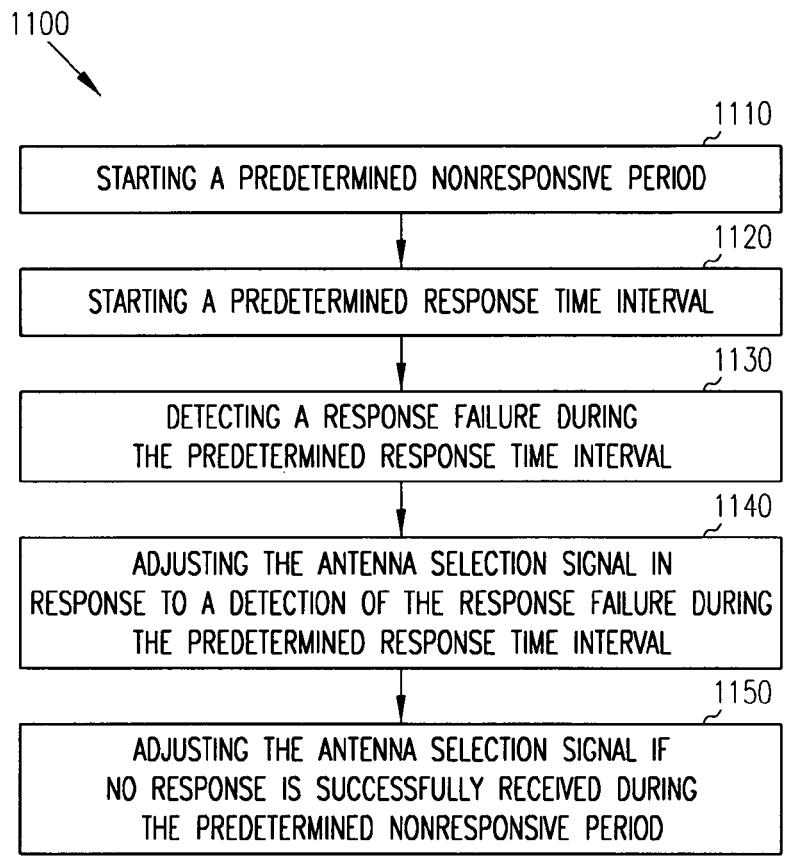
FIG. 11 is a flow chart illustrating an embodiment of a method for adjusting an antenna selection signal.

FIG. 11 is a flow chart illustrating an embodiment of a method 1100 for adjusting the antenna selection signal. Method 1100 is a specific embodiment of method 1000. In a specific embodiment, method 1100 is performed by antenna control circuit 432.

A predetermined nonresponsive period is started at 1110, during the transmission of a multi-frame message when a response frame is expected to be received according to the predetermined communication protocol. The transmission of the multi-frame message is performed using a first antenna of the diversity antenna system. The response frame is expected to be received after two or more outgoing data frames of the multi-frame message are transmitted using the first antenna. In one embodiment, the predetermined nonresponsive period is in a range of approximately 50 milliseconds to 1 second, with 100 milliseconds being a specific example.

A predetermined response time interval is started at 1120, during the transmission of the multi-frame message when the response frame is expected to be received and when each of one or more subsequent response frames, if any, is expected to be received. In one embodiment, the predetermined response time interval is in a range of approximately 4 milliseconds to 1 second, with approximately 100 milliseconds being a specific example. In one embodiment, the predetermined response time interval is limited by the time interval between the end of the transmission of an outgoing data frame and the beginning of the transmission of the next outgoing data frame.

A response failure is detected during the predetermined response time interval at 1130. The response failure is a data transmission error associated with a response frame. In one embodiment, the response frame is detected during the predetermined response time interval. The response failure is detected if the response frame is not detected during the predetermined response time interval. In another embodiment, a comma indicative of a receipt of the response frame is detected during the predetermined response time interval. The response failure is detected if the comma is not detected during the predetermined response time interval. In another embodiment, a CRC failure in the response frame is detected during the predetermined response time interval. The response failure is detected if the CRC failure is detected during the predetermined response time interval. In another embodiment, one or more of the response frame, the comma, and the CRC failure are detected. The response failure is detected if the response frame is not detected, or if the comma is not detected, or if the CRC failure is detected, during the predetermined response time interval.

The antenna selection signal is adjusted for selecting a different antenna of the diversity antenna system to be the active antenna at 1140, if the response failure is detected during the predetermined response time interval. When two or more response frames are expected to be received during the transmission of the multi-frame message, the predetermined response time interval is started when each response frame is expected to be received, and the antenna selection signal is adjusted for selecting a different antenna if the response failure is detected during the predetermined response time interval.

The antenna selection signal is adjusted for selecting a second antenna of the diversity antenna system at 1150, when the predetermined nonresponsive period expires without successful receipt of any response frame. The second antenna is an antenna different from the first antenna. That is, if none of the incoming data frames is received without the data transmission error during the predetermined nonresponsive period, a different antenna is selected for repeating the transmission of the multi-frame message or performing the transmission of another multi-frame message.

Figure 12:
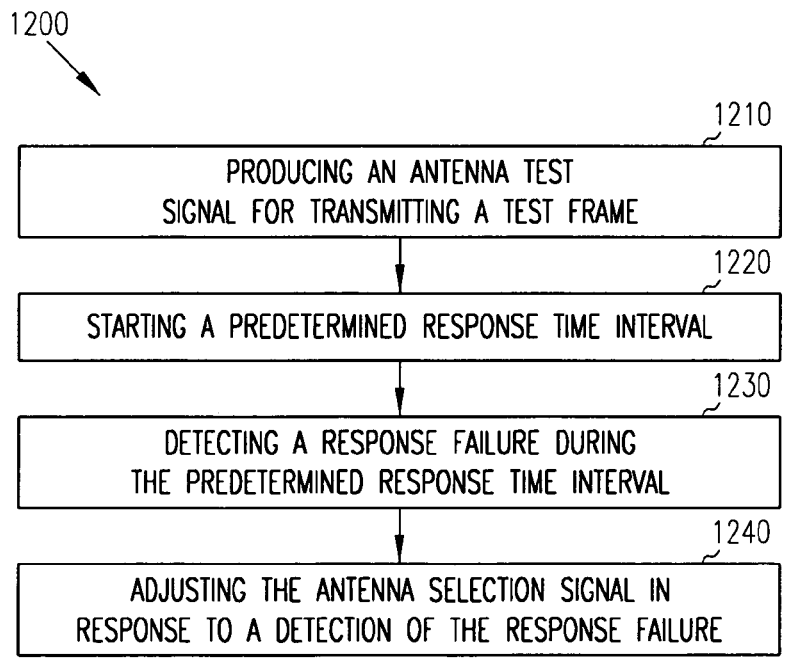
FIG. 12 is a flow chart illustrating an embodiment of another method for adjusting the antenna selection signal.

FIG. 12 is a flow chart illustrating an embodiment of a method 1200 for adjusting the antenna selection signal. Method 1200 is another specific embodiment of method 1000. In a specific embodiment, method 1200 is performed by antenna control circuit 632.

An antenna test signal is produced at 1210, prior to the transmission of the multi-frame message. The antenna test signal cause a test frame to be transmitted to the implantable medical device, which transmits a response frame after receiving the test frame. The predetermined response time interval is started at 1220, following the transmission of the test frame. The response failure is detected during the predetermined response time interval at 1230. The antenna selection signal is adjusted for selecting a different antenna of the diversity antenna system to be the active antenna when the response failure is detected at 1240. In one embodiment, method 1200 is repeated for all the antennas of the diversity antenna system. In another embodiment, method 1200 is repeated with another antenna only if the response failure is detected with the currently active antenna. In another embodiment, if the response failure is detected with the currently active antenna, a different antenna is assumed to be associated with acceptable quality of the incoming signal and is therefore selected.

Figure 13:
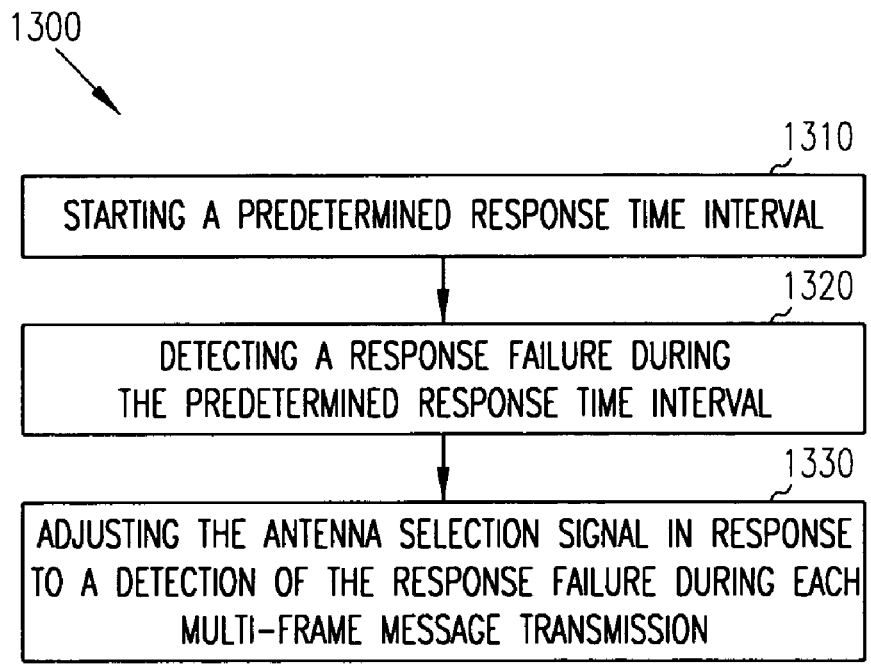
FIG. 13 is a flow chart illustrating an embodiment of another method for adjusting the antenna selection signal.

FIG. 13 is a flow chart illustrating an embodiment of a method 1300 for adjusting the antenna selection signal. Method 1300 is another specific embodiment of method 1000. In a specific embodiment, method 1300 is performed by antenna control circuit 732.

The predetermined response time interval is started at 1310, during the transmission of the multi-frame message when a response frame is expected to be received. The response failure is detected during the predetermined response time interval at 1320. The antenna selection signal is adjusted for selecting a different antenna of the diversity antenna system to be the active antenna after the transmission of the multi-frame message if the response failure is detected during the transmission of the multi-frame message at 1330. When two or more response frames are expected to be received during the transmission of the multi-frame message, a single response failure associated with any of the response frames causes the antenna selection signal to be adjusted for selecting the different antenna to be the active antenna.

Figure 14:
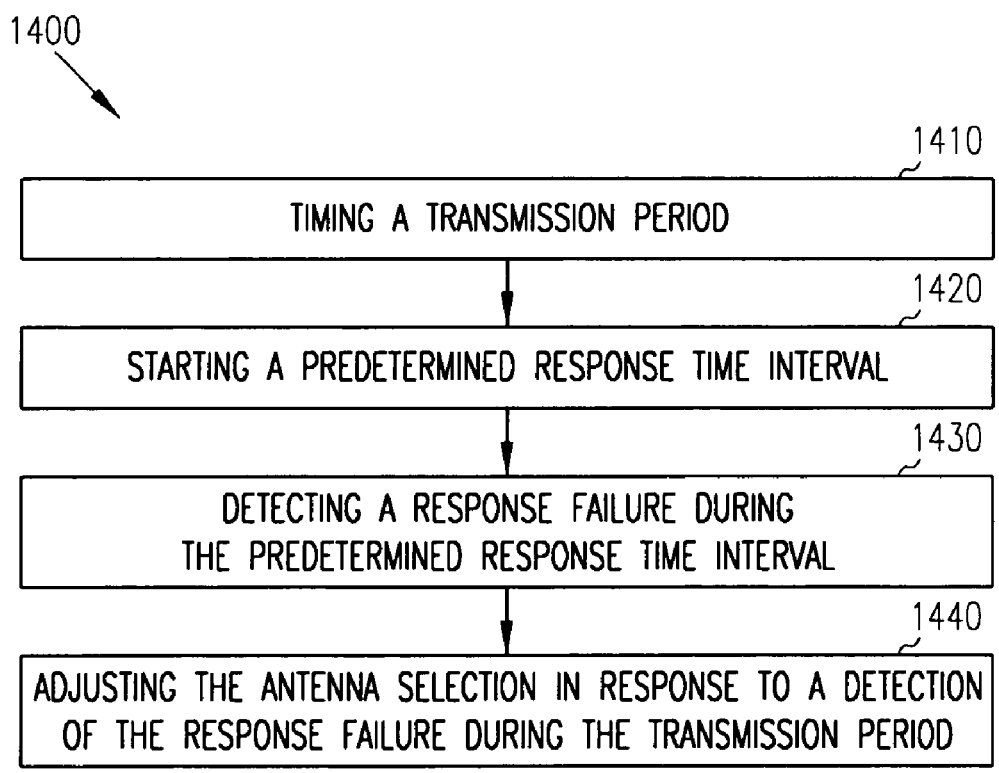
FIG. 14 is a flow chart illustrating an embodiment of another method for adjusting the antenna selection signal.

FIG. 14 is a flow chart illustrating an embodiment of a method 1400 for adjusting the antenna selection signal. Method 1400 is another specific embodiment of method 1000. In a specific embodiment, method 1400 is performed by antenna control circuit 832.

A transmission period is timed at 1410. The transmission period includes a period during which a predetermined number of the outgoing data frames are transmitted. The transmission period is timed repeatedly while the outgoing data frames are transmitted to the implantable medical device. The number of the outgoing data frames in the transmission period is determined based on the predetermined communication protocol. At least one response frame is expected to be received during each transmission period. The predetermined response time interval is started at 1420, during the transmission period when a response frame is expected to be received. The response failure is detected during the predetermined response time interval at 1430. The antenna selection signal is adjusted for selecting a different antenna of the diversity antenna system to be the active antenna at 1440, at the end of the transmission period if the response failure is detection during the transmission period.

Figure 15:
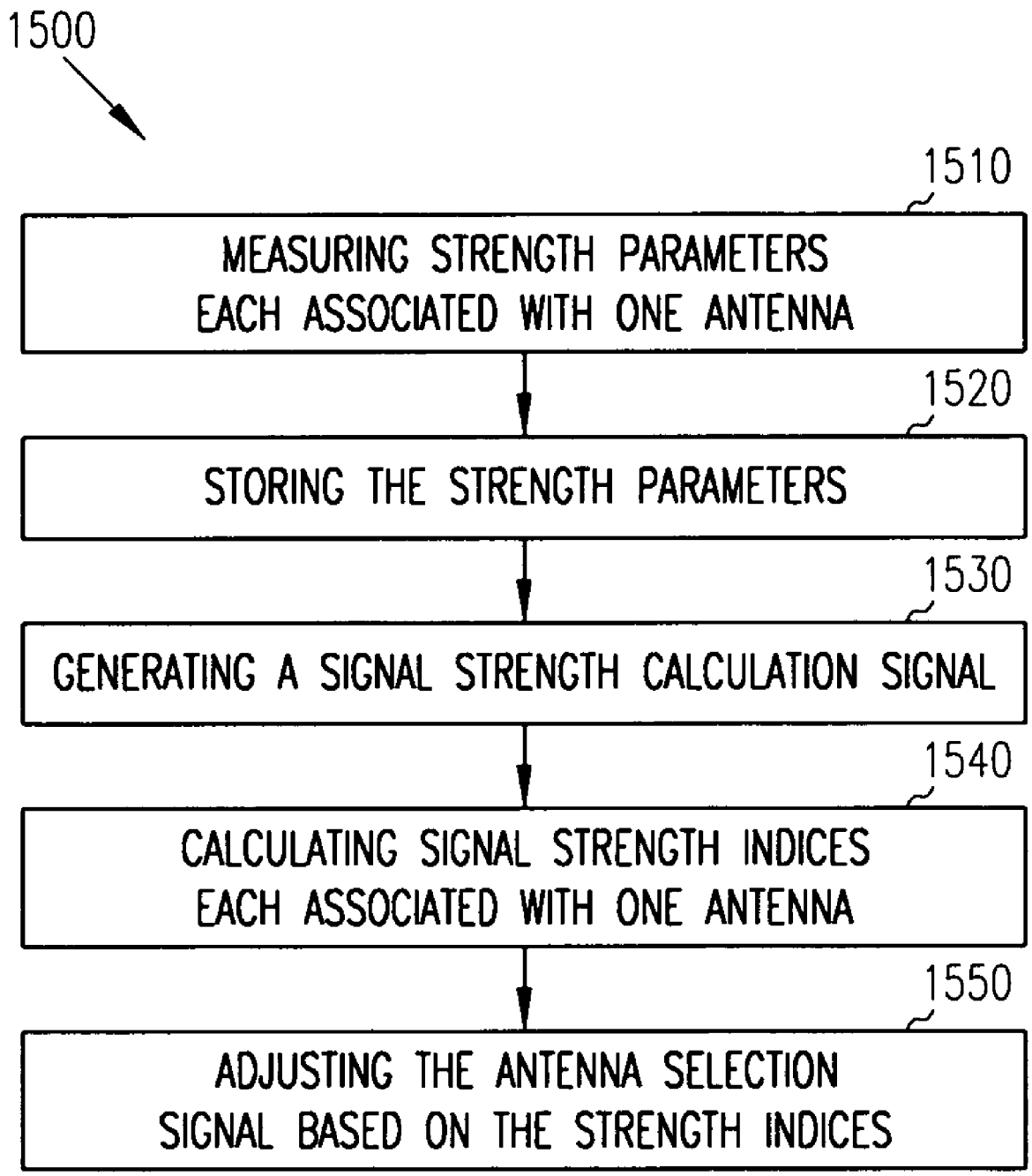
FIG. 15 is a flow chart illustrating an embodiment of another method for adjusting the antenna selection signal.

FIG. 15 is a flow chart illustrating an embodiment of a method 1500 for adjusting the antenna selection signal. Method 1500 is another specific embodiment of method 1000. In a specific embodiment, method 1500 is performed by antenna control circuit 932.

Strength parameters each associated with an antenna are measured at 1510. The strength parameters each represent strength of the incoming signal received by one antenna of the diversity antenna system. Examples of the strength parameter include amplitude and power of the incoming signal. The strength parameters are stored at 1520. Each stored strength parameter is time stamped to indicate when that strength parameter was measured. Prior to the transmission of a multi-frame message, a signal strength calculation signal is generated at 1530. In response to the signal strength calculation signal, signal strength indices are calculated at 1540. The signal strength indices are each associated with one antenna of the diversity antenna system and is calculated based on the strength parameter and a weighting factor. The weighting factor is a function of the time elapsed since the measurement of the strength parameter. The antenna selection signal is adjusted for selecting an antenna of the diversity antenna system to be the active antenna based on the signal strength indices at 1550. In one embodiment, the antenna selection signal is adjusted for selecting the antenna associated with the highest signal strength index, i.e., associated with the strongest incoming signal strength as recently measured.

Methods 1100, 1200, 1300, 1400, and 1500 are exemplary specific embodiments illustrating how the assessment of the quality of the incoming signal is timed and performed and how the antenna selection signal is adjusted based on the assessed quality of the incoming signal. In various embodiments, these specific embodiments may be combined, and other specific embodiments may be employed, as determined by one skilled in the art upon reading and understanding this document. In general, the quality of the incoming signal is assessed using any viable method, and an antenna of the diversity antenna system is selected for being the active antenna based on the quality of the incoming signal assessed for this antenna or for a different antenna.

It is to be understood that the above detailed description is intended to be illustrative, and not restrictive. For example, the implantable medical device can be any implantable medical device capable of communicating with an external system or device via RF telemetry. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system for communicating with an implantable medical device, the system comprising:
   a diversity antenna system including a plurality of antennas configured to transmit an outgoing signal to the implantable medical device and to receive an incoming signal from the implantable medical device;
   a transceiver adapted to transmit outgoing data frames by modulating the outgoing signal and to receive incoming data frames by demodulating the incoming signal;
   an antenna interface circuit coupled between the diversity antenna system and the transceiver, the antenna interface circuit including a switch circuit adapted to connect an antenna of the diversity antenna system to the transceiver according to an antenna selection signal; and
   an antenna control circuit adapted to produce the antenna selection signal, the antenna control circuit including:
   an incoming signal monitoring timer adapted to generate incoming signal monitoring signals based on a predetermined communication protocol;
   an incoming signal monitoring circuit coupled to the incoming signal monitoring timer, the incoming signal monitoring circuit adapted to produce an indication of quality of the incoming signal by detecting at least one measure of quality of the incoming signal in response to each of the incoming signal monitoring signals; and
   an antenna selector coupled to the incoming signal monitoring circuit and the switch circuit, the antenna selector adapted to adjust the antenna selection signal based on the indication of quality of the incoming signal.

2. The system of claim 1, wherein the switch circuit is adapted to connect the antenna of the diversity antenna system to the transceiver for transmitting the outgoing signal and receiving the incoming signal.

3. The system of claim 1, wherein the transceiver is adapted to transmit multi-frame messages each including a plurality of data frames of the outgoing data frames.

4. The system of claim 3, wherein the incoming signal monitoring timer includes a signal strength calculation timer adapted to generate a signal strength calculation signal prior to a transmission of one of the multi-frame messages.

5. The system of claim 4, wherein the incoming signal monitoring circuit comprises:
   a signal strength detector to measure strength parameters each representative of strength of the incoming signal associated with one antenna of the diversity antenna system;
   a signal strength storage circuit to store the strength parameters; and
   a signal strength calculator to calculate signal strength indices each associated with one antenna of the diversity antenna system based on the strength parameters and weighting factors each associated with one of the strength parameters and related to a timing of the measurement of that one of the strength parameters in response to the signal strength calculation signal.

6. The system of claim 5, wherein the antenna selector is adapted to adjust the antenna selection signal for connecting an antenna of the diversity antenna system to the transceiver based on the signal strength indices.

7. The system of claim 3, wherein the incoming signal monitoring timer comprises a response timer to start a predetermined response time interval when a response frame is expected to be received according to the predetermined communication protocol, the response frame being one of the incoming data frames and responding to one or more frames of the outgoing data frames transmitted to the implantable medical device, and wherein the incoming signal monitoring circuit comprises a response failure detector adapted to detect a response failure during the predetermined response time interval, the response failure being a data transmission error associated with the response frame.

8. The system of claim 7, wherein the response failure detector comprises a lack-of-response detector adapted to detect the response frame during the predetermined response time interval, and the response failure is detected if the response frame is not detected during the predetermined response time interval.

9. The system of claim 7, wherein the response failure detector comprises a lack-of-comma detector adapted to detect a comma indicative of a receipt of the response frame during the predetermined response time interval, and the response failure is detected if the comma is not detected during the predetermined response time interval.

10. The system of claim 7, wherein the response failure detector comprises a cyclic redundancy check (CRC) failure detector adapted to detect a CRC failure in the response frame during the predetermined response time interval, and the response failure is detected if the CRC failure is detected during the predetermined response time interval.

11. The system of claim 7, wherein the antenna control circuit further comprises a nonresponsive period timer to start a predetermined nonresponsive period during a transmission of one of the multi-frame messages with a first antenna of the diversity antenna system connected to the transceiver when the response frame is expected to be received, and wherein the response timer is adapted to start the predetermined response time interval during the transmission of the one of the multi-frame messages when the response frame is expected to be received and when each of one or more subsequent response frames is expected to be received, the subsequent response frame each being one of the incoming data frames and responding to one or more frames of the outgoing data frames transmitted to the implantable medical device.

12. The system of claim 11, wherein the antenna selector is adapted to adjust the antenna selection signal for connecting a different antenna of the diversity antenna system to the transceiver if the response failure is detected during the predetermined response time interval and adapted to adjust the antenna selection signal for connecting a second antenna of the diversity antenna system to the transceiver when the predetermined nonresponsive period expires if none of the incoming data frames is received without the data transmission error during the predetermined nonresponsive period.

13. The system of claim 7, wherein the antenna control circuit further comprises a test frame generator to produce an antenna test signal causing the transceiver to transmit a test frame of the outgoing data frames prior to a transmission of one of the multi-frame messages, and wherein the response timer is adapted to start the predetermined response time interval following the transmission of the test frame.

14. The system of claim 13, wherein the antenna selector is adapted to adjust the antenna selection signal for connecting a different antenna of the diversity antenna system to the transceiver if the response failure is detected during the predetermined response time interval.

15. The system of claim 7, wherein the response timer is adapted to start the predetermined response time interval during a transmission of one of the multi-frame messages when the response frame is expected to be received.

16. The system of claim 15, wherein the antenna selector is adapted to adjust the antenna selection signal for connecting a different antenna of the diversity antenna system to the transceiver after the transmission of the one of the multi-frame messages if the response failure is detected during the transmission of the one of the multi-frame messages.

17. The system of claim 7, wherein the antenna control circuit further comprises a transmission period timer to time transmission periods each including a period during which a predetermined number of data frames of the outgoing data frames are transmitted, and wherein the response timer is adapted to start the predetermined response time interval during each of the transmission periods when the response frame is expected to be received.

18. The system of claim 17, wherein the antenna selector is adapted to adjust the antenna selection signal for connecting a different antenna of the diversity antenna system to the transceiver at an end of the each of the transmission periods if the response failure is detected during the each of the transmission periods.

19. A method for operating a telemetry system communicating with an implantable medical device, the method comprising:
transmitting an outgoing signal to the implantable medical device and receiving an incoming signal from the implantable medical device using a diversity antenna system including a plurality of antennas, wherein transmitting the outgoing signal includes transmitting outgoing data frames by modulating the outgoing signal, and receiving the incoming signal includes receiving incoming data frames by demodulating the incoming signal;
selecting an antenna of the diversity antenna system to be an active antenna according to an antenna selection signal, the active antenna used for transmitting the outgoing signal and receiving the incoming signal;
generating incoming signal monitoring signals based on a predetermined communication protocol;
producing an indication of quality of the incoming signal by detecting at least one measure of quality of the incoming signal in response to each of the incoming signal monitoring signals; and
adjusting the antenna selection signal based on the indication of quality of the incoming signal.

20. The method of claim 19, wherein transmitting the outgoing data frames comprises transmitting multi-frame messages each including a plurality of data frames of the outgoing data frames.

21. The method of claim 20, wherein generating the incoming signal monitoring signals comprises generating a signal strength calculation signal prior to a transmission of one of the multi-frame messages.

22. The method of claim 21, wherein producing the indication of quality of the incoming signal comprises:
measuring strength parameters each representative of strength of the incoming signal associated with one antenna of the diversity antenna system;
storing the measured strength parameters; and
calculating signal strength indices each associated with one antenna of the diversity antenna system based on the strength parameters and weighting factors each associated with one of the strength parameters and related to a timing of the measurement of that one of the strength parameters in response to the signal strength calculation signal.

23. The method of claim 22, wherein adjusting the antenna selection signal comprises adjusting the antenna selection signal for selecting an antenna of the diversity antenna system to be the active antenna based on the signal strength indices.

24. The method of claim 20, wherein generating the incoming signal monitoring signals comprises starting a predetermined response time interval when a response frame is expected to be received according to the predetermined communication protocol, the response frame being one of the incoming data frames and responding to one or more frames of the outgoing data frames transmitted to the implantable medical device, and wherein detecting the at least one measure of quality of the incoming signal comprises detecting a response failure during the predetermined response time interval, the response failure being a data transmission error associated with the response frame.

25. The method of claim 24, wherein detecting the response failure comprises detecting the response frame during the predetermined response time interval, and wherein the response failure is detected if the response frame is not detected during the predetermined response time interval.

26. The method of claim 24, wherein detecting the response failure comprises detecting a comma indicative of a receipt of the response frame during the predetermined response time interval, and wherein the response failure is detected if the comma is not detected during the predetermined response time interval.

27. The method of claim 24, wherein detecting the response failure comprises detecting a cyclic redundancy check (CRC) failure in the response frame during the predetermined response time interval, and wherein the response failure is detected if the CRC failure is detected during the predetermined response time interval.

28. The method of claim 24, further comprising starting a predetermined nonresponsive period during a transmission of one of the multi-frame messages using a first antenna of the diversity antenna system selected to be the active antenna when the response frame is expected to be received, and wherein starting the predetermined response time interval comprises starting the predetermined response time interval during the transmission of the one of the multi-frame messages when the response frame is expected to be received and when each of one or more subsequent response frames is expected to be received, the one or more subsequent response frames each being one of the incoming data frames and responding to one or more frames of the outgoing data frames transmitted to the implantable medical device.

29. The method of claim 28, wherein adjusting the antenna selection signal comprises adjusting the antenna selection signal for selecting a different antenna of the diversity antenna system to be the active antenna if the response failure is detected during the predetermined response time interval.

30. The method of claim 29, wherein adjusting the antenna selection signal further comprises adjusting the antenna selection signal for selecting a second antenna of the diversity antenna system to be the active antenna when the predetermined nonresponsive period expires if none of the incoming data frames is received without the data transmission error during the predetermined nonresponsive period.

31. The method of claim 24, further comprising producing an antenna test signal causing a transmission of a test frame of the outgoing data frames prior to a transmission of one of the multi-frame messages, and wherein starting the predetermined response time interval comprises starting the predetermined response time interval following the transmission of the test frame.

32. The method of claim 31, wherein adjusting the antenna selection signal comprises adjusting the antenna selection signal for selecting a different antenna of the diversity antenna system to be the active antenna when the response failure is detected during the predetermined response time interval.

33. The method of claim 24, wherein starting the predetermined response time interval comprises starting the predetermined response time interval during a transmission of one of the multi-frame messages when the response frame is expected to be received.

34. The method of claim 33, wherein adjusting the antenna selection signal comprises adjusting the antenna selection signal for selecting a different antenna of the diversity antenna system to be the active antenna after the transmission of the one of the multi-frame messages if the response failure is detected during the transmission of the one of the multi-frame messages.

35. The method of claim 24, further comprising timing transmission periods each including a period during which a predetermined number of data frames of the outgoing data frames are transmitted, and wherein starting the predetermined response time interval comprises starting the predetermined response time interval during each of the transmission periods when the response frame is expected to be received.

36. The method of claim 35, wherein adjusting the antenna selection signal comprises adjusting the antenna selection signal for selecting a different antenna of the diversity antenna system to be the active antenna at an end of the each of the transmission periods if the response failure is indicated during the each of the transmission periods.

* * * * *

UNITED STATES PATENT AND TRADEMARK OFFICE
CERTIFICATE OF CORRECTION

PATENT NO.         : 7,392,092 B2
APPLICATION NO. : 11/068476
DATED              : June 24, 2008
INVENTOR(S)        : Hui Li et al.

It is certified that error appears in the above-identified patent and that said Letters Patent is hereby corrected as shown below:

In column 1, line 15, delete "TN" and insert -- IN --, therefor.

Signed and Sealed this

Second Day of September, 2008

JON W. DUDAS
*Director of the United States Patent and Trademark Office*